(12) United States Patent
Bartholeyns et al.

(10) Patent No.: US 6,399,372 B1
(45) Date of Patent: Jun. 4, 2002

(54) MONOCYTE DERIVED CELLS WITH IMMUNOSTIMULATING PROPERTIES, THEIR PREPARATION AND USES

(75) Inventors: Jacques Bartholeyns, Bures-sur-Yvette; Mohamed Chokri, Paris, both of (FR); Nathalie Latour, Braine l'Alleud (BE)

(73) Assignee: I.D.M. Immuno-Designed, Paris (FR)

( * ) Notice: Subject to any disclaimer, the term of this patent is extended or adjusted under 35 U.S.C. 154(b) by 0 days.

(21) Appl. No.: 09/647,534

(22) PCT Filed: Mar. 29, 1999

(86) PCT No.: PCT/EP99/02106

§ 371 (c)(1),
(2), (4) Date: Oct. 2, 2000

(87) PCT Pub. No.: WO99/50391

PCT Pub. Date: Oct. 7, 1999

(30) Foreign Application Priority Data

Mar. 30, 1998 (EP) .......................................... 98400742

(51) Int. Cl.⁷ .............................. C12N 5/00; C12N 5/02
(52) U.S. Cl. ....................................... 435/325; 435/375
(58) Field of Search ...................... 514/17, 8; 435/366, 435/325; 424/184.1

(56) References Cited

U.S. PATENT DOCUMENTS

| | | | |
|---|---|---|---|
| 5,679,347 A | * 10/1997 | Porcelli et al. | 424/184.1 |
| 5,962,320 A | * 10/1999 | Robinson | 435/366 |
| 6,165,979 A | * 12/2000 | Kozhemyakin et al. | 514/17 |

FOREIGN PATENT DOCUMENTS

| | | |
|---|---|---|
| EP | 0 808 897 | 11/1997 |
| WO | WO 82/02338 | 7/1982 |
| WO | WO 92/05793 | 4/1992 |
| WO | WO 92/21691 | 12/1992 |
| WO | WO 94/26875 | 11/1994 |
| WO | WO 96/22781 | 8/1996 |
| WO | WO 97/10002 | 3/1997 |
| WO | WO 97/21444 | 6/1997 |

OTHER PUBLICATIONS

Haddada H. et al, "Efficient Adenovirus–Mediated Gene Transfer into Human Blood Monocyte–Derived Macrophages", Biochem. Biophys. Res. Comm., vol. 195, pp. 1174–1183 (1993).*

Lopez M. et al., "Autologous lymphocytes prevent the death of monocytes in culture and promote, as do GM–CSF, IL–3 and M–CSF, their differentiation into macrophages", J. Immunol. Methods, vol. 159, pp. 29–38 (1993).*

Demain A. et al, "Manual of Industrial Microbiology and Biotechnology", p. 259. American Society for Microbiology, Washington, D.C. (1996).*

Coligan J. E. et al., "Current Protocols in Immunology", vol. 2, pp. 10.15.1–10.15.3, John Wiley & Sons, Inc. (1992).*

J. Bartholeyns et al., "Immune therapy with Macrophages: Present Status . . . ", *Immunobiol.*, vol. 195, Oct. 1996, pp. 550–562.

J. Bartholeyns et al., "immune Control of Neoplasia by adoptive Transfer of Macrophages Potentiality for . . . ", *Anticancer Research*, vol. 14, No. 6B, Nov. 1994, pp.2673–2676.

H. Okamoto et al., "Possible Involvement of Adenosine 3':5'–cyclic monophosphate and extracellular calcium ions in histamine . . . ", *Immunology*, vol. 70, No. 2, Jun. 1990, pp. 186–190.

B.S. Polla et al., "Differential Induction of Stress Proteins and Functional Effects of Heat Shock in Human Phagocytes", *Inflammation*, vol. 19, No. 3, 1995, pp. 363–378.

E. Mariethoz et al., "exposure of Monocytes to Heat Shock Does Not Increase Class II Expression But Modulates Antigen–dependent T Cell Responses", *International Immunology*, vol. 6, No. 6, 1994, pp. 925–930.

* cited by examiner

*Primary Examiner*—Kenneth R. Horlick
*Assistant Examiner*—Teresa Strezecka
(74) *Attorney, Agent, or Firm*—Young & Thompson

(57) ABSTRACT

The invention relates to stimulated monocyte derived cells presenting the following characteristics: 1) increased release, with respect to normal monocyte derived cells, of for instance PDGF (platelet derived growth factor), and increased presence, on their membranes, with respect to normal monocyte derived cells, of for instance CD1α, and/or: 2) presence in their nucleus of at least one exogenous nucleic acid which has been integrated in the absence of the monocyte derived cell division. These stimulated monocyte derived cells can be the active substance of pharmaceutical compositions.

19 Claims, No Drawings

MONOCYTE DERIVED CELLS WITH IMMUNOSTIMULATING PROPERTIES, THEIR PREPARATION AND USES

The invention relates to stimulated monocyte derived cells, processes for their preparation, and pharmaceutical compositions containing the same.

It has long been established that macrophages have a primary role in wound and tissue repair (see for example Wong and Wahl, Inflammation and repair, in Handbook of Exp Pharmacol, 95:509–548, 1990). They are inducers and regulators of healing; they favor angiogenesis and recruit cells which will complete wound repair. After a tissue has been injured (burn, ulcers, wounds, trauma, mucosal damage, infarcts or even reconstructive surgery), macrophages called locally clean the wound by elimination of the necrotic debris formed by dead cells (by phagocytosis and proteolysis). At the same time macrophages, activated locally by this phagocytosis, actively release growth factors, monokines and chemokines. These autologous factors stimulate surrounding cells to multiply and to migrate towards the wound and to replace the dead cells.

Macrophages play a major role in the antitumoral response, and they are able to be activated by immunological activators against cancer cells (Adams D. and Hamilton T.: "Activation of macrophages for tumor cell kill: effector mechanism and regulation"; in Heppner & Fulton (eds), Macrophages and cancer. CRC Press, 1988, p. 27; Fidler M. Macrophages and metastases. A biological approach to cancer therapy. Cancer Res. 45: 4714, 1985).

Furthermore, macrophages, or other cells derived from monocytes or from their precursors, with their strong capacity for endocytosis, digestion, and surface antigen presentation, are capable of inducing a specific immune response. In this way, they represent good candidates for the preparation of vaccines, and more specifically cellular autologous vaccines.

Monocytes derived cells (MDCs) are immune cells such as obtained by culture of blood mononuclear cells in non adherent gas permeable plastic or Teflon bags for 5 to 10 days at 37° C. in $O_2/CO_2$ atmosphere. Their culture medium (RPMI. IMDM, AIM5 (Gibco) or X-VIVO (Biowhittaker)) contains eventually cytokines or ligands as defined in patents no PCT/EP93101232, no WO94/26875 or EP 97/02703 or in the articles mentioned below:

"Autologous lymphocytes prevent the death of monocytes in culture and promote, as do GM-CSF, IL-3 and M-CSF, their differentiation into macrophages". (Lopez M., Martinache Ch., Canepa S., Chokri M., Scotto F., Bartholeyns J.; J. of Immunological Methods, 159: 29–38, 1993);

"Immune therapy with macrophages: Present status and critical requirements for implementation" (Bartholeyns J., Romet-Lemonne J-L., Chokri M., Lopez M.; Immunobiol., 195: 550–562, 1996);

"In vitro generation of CD83+ human blood dendritic cells for active tumor immunotherapy" (Thurnher M., Papesh C., Ramoner R., Gastlt G. and al.; Experimental Hematology, 25:232–237, 1997);

"Dendritic cells as adjuvants for immune-mediated resistance to tumors" (Schuler G. and Steinman R. M.; J. Exp. Med., 186:1183–1187, 1997).

All these patent applications and articles are included herein for references.

They can be activated by IFN-γ at the end of culture to obtain in particular cytotoxic macrophages. They can be entrifuged to be concentrated and purified before resuspension in isotonic solution.

Monocyte derived cells (MDCs) can either be killer macrophages, phagocytozing cells, growth factors and cytokines releasing cells, or dendritic cells according to their conditions of differentiation. Dendritic cells can for example be obtained as described in "In vitro generation of CD83+ human blood dendritic cells for active tumor immunotherapy" (Thurnher M., Papesh C., Ramoner R., Gastlt G. and al.; Experimental Hematology, 25:232–237, 1997) and "Dendritic cells as adjuvants for immune-mediated resistance to tumors" (Schuler G. and Steinman R. M.; J. Exp. Med., 186:1183–1187, 1997), and EP 97/092703.

Mature dendritic cells are very potent antigen presenting cells to initiate an immune response. The dendritic cells can be characterized by the induction of T cell proliferation and by their phenotype (presence of CD80, CD86, CD83, MHC-I, MHC-II on their membranes).

The dendritic cells play an important role, but are difficult to obtain in large quantities, necessary for therapeutic purpose in particular because of the required presence of multiple cytokines. Moreover, the dendritic cells obtained according to standard procedures are not stimulated and therefore do not present direct anti-tumoral or tissue repair properties.

One of the aim of the invention, is to provide stimulated monocyte derived cells having enhanced biological activities as described above, when compared to monocyte derived cells described until now.

Another aim of the invention is to provide processes for the preparation of said stimulated monocyte derived cells.

Another aim of the invention is to provide new pharmaceutical compositions containing said stimulated monocyte derived cells.

Another aim of the invention is to provide new methods for the treatment of tissue injuries.

Another aim of the invention is to provide new methods for the treatment or vaccination against tumors or infectious (bacterial or viral) diseases.

Another aim of the invention is to provide new methods for gene therapy.

The invention relates to stimulated monocyte derived cells presenting the following characteristics:

1)—increased release, with respect to normal monocyte derived cells, of at least one of the following polypeptides, proteins or compounds:

| | |
|---|---|
| PDGF | (platelet derived growth factor) |
| IGF1 | (insulin growth factor) |
| MDGF | (macrophage derived growth factor) |
| bFGF | (basic fibroblast growth factor) |
| GM-CSF | (granulocyte macrophage - colony stimulating factor) |
| heat shock or stress proteins, | |
| chemokines and monokines such as IL12 and IFNγ | | enzymes or enzyme inhibitors,
complement components,
transfer proteins,
peroxides, NO (nitrous oxide),
bioactive lipids,
hormones,
and
increased presence, on their membranes, with respect to normal monocyte derived cells, of at least one of the following activation markers: CD1α, CD11a, CD80, CD83, CD86, MHC class I and MHC class II molecules, adhesions, or accessory molecules for immunostimulation such as ICAM, or CD40, and/or
2) presence in their nucleus of at least one exogenous nucleic acid which has been integrated in the absence of the monocyte derived cell division.

The expression normal monocyte derived cells correspond to monocytes cultured in defined media or in the presence of cytokines which have not been specifically stressed and therefore which do not release increased levels of immunostimnulatory proteins or compounds and simultaneously do not express markedly increased levels of MHC and accessory molecules on their membranes.

NO is usually not released due to NO synthase suppression, but, in the case of the invention, NO synthase is uninhibited which causes release of NO.

Monocytes derived cells can be obtained for instance from blood derived monocytes purified and cultured in the presence of GM-CSF and another cytokine, such as IL-4 or IL-13.

The invention relates more particularly to stimulated monocyte derived cells as described above, wherein the released polypeptides, proteins and compounds are those listed on Table 1.

According to an advantageous embodiment, tie activation markers are present in an amount of at least about 1000 molecules/cells.

This can be measured by flow cytometry.

In a particular embodiment of the invention, the monocyte derived cells as described above contain exogenous compounds in their cytoplasm such as drugs, protein and growth factors of interest.

In another embodiment, the monocyte derived cells as described above contain in their cytoplasm exogenous DNA coding for a protein of interest.

It should be made clear that depending upon the nature of the physical stress, either the DNA contained in the cytoplasm of said monocyte derived cells remain in the cytoplasm after the physical stress, or there is an uptake of said exogenous DNA by their nucleus which is made possible by the physical stress.

The physically stimulated monocyte derived cells of the invention are particularly suited for vaccination purpose since they express at the same time the antigen introduced, increased membrane levels of MHC molecules and accessory molecules to interact with lymphocytes and they release increased amounts of TH1 type (e.a. IL-12) cytokines.

According to an advantageous embodiment, the stimulated monocyte derived cells of the invention, present the following characteristics:

1) increased release, with respect to normal monocyte derived cells, of at least one of the following polypeptides or proteins:

| | |
|---|---|
| PDGF | (platelet derived growth factor) |
| IGF1 | (insulin growth factor) |
| MDGF | (macrophage derived growth factor) |
| bFGF | (basic fibroblast growth factor) |
| GM-CSF | (granulocyte macrophage - colony stimulating factor) |
| heat shock or stress proteins, such as HSP70, HSP90, GP96, | |
| chemokines and monokines such as IL12 and IFNγ | | and
increased presence, on their membranes, with respect to normal monocyte derived cells, of at least one of the following activation markers: CD1α, CD11, CD80, CD83, CD86, MHC class I and MHC class II molecules, adhesions, or accessory molecules for immunostimulation such as ICAM, or CD40, and/or
2) presence in their nucleus of at least one exogenous nucleic acid which has been integrated in the absence of the monocyte derived cell division.

According to an advantageous embodiment of the invention, said activation markers are present in an amount of at least about 1000 molecules/cell.

This can be measured by flow cytometry.

Advantageous stimulated monocyte derived cells according to the invention present at least one of the following characteristics:

increased release, with respect to normal monocyte derived cells, of at least one of the following polypeptides, proteins or compounds:
PDGF
IGF1
MDGF
bFGF
GM-CSF
heat shock or stress proteins
chemokines and monokines such as IL12 and IFNγ
enzymes or enzyme inhibitors
complement components
transfer proteins
peroxides, NO (nitrous oxide),
bioactive lipids
hormones
and
increased presence, on their membranes, with respect to normal monocyte derived cells, of at least one of the following activation markers: CD1α, CD11a, CD80, CD83, CD86, MHC class I and MHC class II molecules, adhesions, or accessory molecules for immunostimulation such as ICAM, or CD40.

According to an advantageous embodiment of the invention, the above polypeptides, proteins or compounds are present in an amount higher than about 1 pg/cell/hr. and the above activation markers are present in the range of about $10^3$ to about $10^5$ molecules/cell.

This can be measured by flow cytometry.

Advantageous stimulated monocyte derived cells of the invention present at least one of the following characteristics:

increased release, with respect to normal monocyte derived cells, of at least one of the following polypeptides or proteins:
PDGF
IGF1
MDGF
bFGF
GM-CSF
heat shock or stress proteins
chemokines and monokines such as IL12 and IFNγ
and
increased presence, on their membranes, with respect to normal monocyte derived cells, of one of the following activation markers: CD1α, CD11a, CD80, CD83, CD86, MHC class I and MHC class II molecules, adhesions, or accessory molecules for immunostimulation such as ICAM, or CD40.

According to an advantageous embodiment of the invention, the above polypeptides, proteins or compounds are present in an amount higher than about 1 pg/cell/hr, and the above activation markers are present in the range higher than about $10^3$ and particularly of about $10^3$ to about $10^5$ molecules/cell.

This can be measured by flow cytometry.

The invention relates more particularly to stimulated monocyte derived cells, which present the characteristic of having integrated at least one exogenous nucleic acid in their nucleus in the absence of the monocyte derived cell division.

It is to be reminded that transfer of exogenous nucleic acids in cell nuclei by non viral techniques can be effectively achieved in rapidly dividing cells. In non dividing cells such as those derived from monocytes, the exogenous nucleic acids are internalized in vacuoles or in the cytoplasm, but very low integration in endogenous nucleic acids and expression of the coded peptide occur (<5%). The physical stimulation of the invention allows migration of the exogenous nucleic acids internalized from the cytoplasm to the nucleus and therefore enables increased expression of the transgene.

Advantageous stimulated monocyte derived cells according to the invention, present the following characteristics:
increased release, with respect to normal monocyte derived cells, of at least one of the following polypeptides, proteins or compounds:
PDGF
IGF1
MDGF
bFGF
GM/CSF
heat shock or stress proteins
chemokines and monokines such as IL12 and IFNγ
enzymes or enzyme inhibitors
complement components
transfer proteins
peroxides, NO (nitrous oxide),
bioactive lipids
hormones;
and increased presence, on their membranes, with respect to normal monocyte derived cells, of at least one of the following activation markers: CD1α, CD11a, CD80, CD83, CD86, MHC class I and MHC class II molecules, adhesions, or accessory molecules for immunostimulation such as ICAM, and CD40,
and presence in their nucleus of at least one exogenous nucleic acid which has been integrated in the absence of the monocyte derived cell division.

According to an advantageous embodiment of the invention, the above-mentioned polypeptides, proteins or compounds are present in an amount higher than about 1 pg/cell;hr, and the above-mentioned activation markers are present in the range of about $10^3$ to about $10^5$ molecules/cell.

This can be measured by flow cytometry.

Advantageous stimulated monocyte derived cells of the invention present the following characteristics:
increased release with respect to normal monocyte derived cells of at least one of the following polypeptides or proteins:
PDGF
IGF1
MDGF
bFGF
GM-CSF
heat shock or stress proteins
chemokines and monokines such as IL12 and IFNγ
and increased presence on their membranes with respect to normal monocyte derived cells of at least one of the following activation markers: CD1α, CD11a, CD80, CD83, CD86, MHC class I and MHC class II molecules, adhesions, or accessory molecules for immunostimulation such as ICAM, and CD40,
and presence in their nucleus of at least one exogenous nucleic acid which has been integrated in the absence of the monocyte derived cell division.

According to an advantageous embodiment of the invention, the above-mentioned polypeptides, proteins or compounds are present in an amount higher than about 1 pg/cell/hr, and the above-mentioned activation markers are present in the range of about $10^3$ to about $10^5$ molecules/cell.

The amount of polypeptides, proteins or compounds can be measured by ELISA method and the number of membrane activation markers can be measured by flow cytometry.

The invention also relates to a process for the preparation of monocytes derived cells comprising the step of stimulation of said monocyte derived cells by physical means such as: thermal stress (heating at 40° C. to 50° C. for at least 30 minutes), pressure change (from about 1 bar to about 0.05 bar, or from about 1 bar to about 10 bars), microwaves, electric shock (about 1 to about 10 s at about 250 mV), or electropulsation.

Thermal stress or heat shock is applied as described in: "Differential induction of stress proteins and functional effects of heat shock in human phagocytes." (Polla B. S., Stubbe H., Kantengwa S., Maridonneau-Parini I., Jacquier-Sarlin M. R.—Inflammation, 19:363–378, 1995) or in "Stress-inducible cellular responses" (Feige U., Morimoto R. I., Yahara I., Polla B. S.—BirkhäuserVerlag (Basel, Boston, Berlin), 492p., 1996).

Microwaves are applied under the following conditions: (5 sec to 5 min) 500 to 750 Watts, repeated 1 to 5 times.

Electropulsation (for instance 5 to 10 square electric pulses of 5 millisec at 0.3 to 0.8 kV/cm) allows flux of ions and of nucleic acids and/or protein transporters from the cytoplasm through the nucleus pores. This positive flux is stopped after the pulsation and the exogenous nucleic acid is integrated in nuclear DNA ("Specific electropermeabilization of leucocytes in a blood sample and application to large volumes of cells"; S. Sixou and J. Teissié; Elsevier, Biochimica et Biophysica Acta. 1028:154–160, 1990).

Electric shock is applied as described in "Control by Pulse Parameters of Electric Field-Mediated Gene Transfer in Mammalian Cells" (Hendrick W. et al., Biophysical Journal, Vol. 66:524–531, February 1994).

The process for the preparation of stimulated monocyte derived cells of the invention comprises the following steps:
preparation of monocyte derived cells according to the following method:
1) recovery of blood derived mononuclear cells directly from blood apheresis or from blood bag collection, followed if necessary by centrifugation, to eliminate a substantial part of red blood cells granulocytes and platelets, and collection of peripheral blood leukocytes;
2) washing peripheral blood leukocytes obtained at the preceeding steps for instance by centrifugation (to remove 90% of platelets, red blood cells and debris) to obtain mononuclear cells;
3) resuspension of the total mononuclear cells (monocytes+lymphocytes) obtained at the preceding step in culture medium (AIM-V, RPMI or IMDM type) at $10^6$ to $2.10^7$ cells/ml, possibly completed by cytokines and/or autologous serum, and culture for 5 to 10 days at 37° C. under $O_2/CO_2$ atmosphere in hydrophobic gas permeable bags, to obtain monocyte derived cells and contaminating lymphocytes;
stimulation of said monocyte derived cells by physical means such as: thermal stress (heating at 40° C. to 50°

C. for at least 30 minutes), pressure change (from about 1 bar to about 0.05 bar, or from about 1 bar to about 10 bars), microwaves, electric shock (about 1 to about 10 s at about 250 mV), or electropulsation for a time sufficient to induce the above-mentioned characteristics.

Stimulation of said monocyte derived cells can also be achieved by means of chemicals which cause maturation of said monocyte derived cells, resulting in increased stimulation of cells as described above. Advantageous chemicals are those which are responsible for the production by monocyte derived cells of IFN which endogenously activates the cells (stress signal). This IFN induction can be generated by double stranded RNA (such as poly IC) (polyinosinic-polycytidylic acid) or by bacterial or mycobacterial extracts and particularly bacterial type DNA or corresponding natural or chemically modified oligonucleotides.

The invention also relates to a process for the preparation of stimulated monocyte derived cells, comprising the following steps:

preparation of monocyte derived cells according to the following method:
1) recovery of blood derived mononuclear cells directly from blood apheresis or from blood bag collection, followed if necessary by centrifugation, to eliminate a substantial part of red blood cells granulocytes and platelets, and collection of peripheral blood leukocytes;
2) washing peripheral blood leukocytes obtained at the preceding steps for instance by centrifugation (to remove 90% of platelets, red blood cells and debris) to obtain mononuclear cells;
3) resuspension of the cells (monocytes+lymphocytes) obtained at the preceeding step in culture medium (AIM V, RPMI or IMDM type) at $10^6$ to $2.10^7$ cells/ml, possibly completed by cytokines and/or autologous serum, and culture for 5 to 10 days at 37° C. under $O_2/CO_2$ atmosphere in hydrophobic gas permeable bags, to obtain monocyte derived cells and contaminating lymphocytes;

stimulation of said monocyte derived cells by addition of chemicals which induce endogenous IFN production such as double stranded RNA or bacterial or mycobacterial extracts and particularly bacterial type DNA or corresponding natural or chemically modified oligonucleotides.

It should be noted that the presence of contaminating lymphocytes with the monocyte derived cells during culture and differentiation of the monocytes allows a better control of stimulation and cell recovery through paracrine cellular interactions.

The lymphocytes are segregated from the stimulated monocytes derived cells at the end of the process.

The monocyte derived cells can be for instance prepared according to a method such as described in patents PCT/EP93/01232, WO94/26875 or EP 97/02703 or in the articles mentioned below:

"Autologous lymphocytes prevent the death of monocytes in culture and promote, as do GM-CSF, IL-3 and M-CSF, their differentiation into macrophages". (Lopez M., Martinache Ch., Canepa S., Chokri M., Scotto F., Bartholeyns J.; J. of Immunological Methods, 159:29–38, 1993);

"Immune therapy with macrophages: Present status and critical requirements for implementation" (Bartholeyns J., Romet-Lemonne J-L., Chokri M., Lopez M.; Immunobiol., 195:550–562, 1996);

"In vitro generation of CD83$^+$ human blood dendritic cells for active tumor immunotherapy" (Thurnher M., Papesh C., Ramoner R., Gastlt G. and al.; Experimental Hematology, 25:232–237, 1997);

"Dendritic cells as adjuvants for immune-mediated resistance to tumors" (Schuler G. and Steinman R. M.; J. Exp. Med., 186:1183–1187, 1997).

The monocyte derived cells and contaminating lymphocytes can be treated so as to interiorize drugs, proteins or antigens, by culture of said monocyte derived cells and contaminating lymphocytes for 2 to 24 h, in the presence of drugs, proteins or antigens to interiorize these compounds in said monocyte derived cells.

In a particular embodiment of the invention, the process described above comprises, prior to the step of stimulation, a step of loading the monocyte derived cells with exogenous compounds such as drugs, proteins, growth factors of interest (e.g. by pinocytosis, phagocytosis of particular aggregates, diffusion), or with DNA coding for a protein of interest (i.e. with DNA plasmids, by sugar receptors mediated uptake for glycosylated polylysine-DNA or by lipid-DNA intake). The loaded monocyte derived cells are then stimulated by physical means such as described above, and more particularly by electropulsation which causes the transport of the exogenous compound loaded from the cytoplasm to the nuclei (where they can for example insert in DNA).

The process of the invention, in an advantageous embodiment, comprises, after the step of stimulation, the additional step of centrifugation of the stimulated monocyte derived cells at a temperature enabling cell preservation, for instance at 4° C., and resuspension, for instance in isotonic medium containing autologous serum.

The process of the invention, according to another advantageous embodiment, comprises, after the step of stimulation, the additional steps of:

centrifugation of the stimulated monocyte derived cells at a temperature enabling cell preservation, for instance at 4° C., and resuspension, for instance in isotonic medium containing autologous serum, and freezing at a temperature at least of –80° C. aliquots of the stimulated monocyte derived cells obtained at the preceding step, with the addition of a cryopreservative such as polyethyleneglycol, glycerol, DMSO (dimethylsulfoxide).

According to an advantageous embodiment, the process for the preparation of stimulated monocyte derived cells according to the invention, comprises the following steps:

loading the monocyte derived cells thus obtained with an exogenous nucleic acid through endocytosis targeting their mannose and/or Fc receptors, or via pinocytosis of macromolecular nucleic acid aggregates, and submission of the monocyte derived cells obtained at the preceding step to physical stress such as electropulsation, for example about 1 to about 10 pulses of about 5 msecs at about 0.3 to about 1 kV/cm, enabling intracellular transfer of the exogenous nucleic acid into the nucleus and integration into the DNA of the nucleus.

According to another advantageous embodiment of the invention, the process for the preparation of stimulated monocyte derived cells comprises the following steps:

preparation of monocyte derived cells according to the following method:
1) recovery of blood derived mononuclear cells directly from blood apheresis or from blood bag collection, followed if necessary by centrifugation, to eliminate a substantial part of red blood cells granulocytes and platelets, and collection of peripheral blood leukocytes;

2) washing peripheral blood leukocytes obtained at the preceding steps for instance by centrifugation (to remove 90% of platelets, red blood cells and debris) to obtain mononuclear cells;

3) resuspension of the total mononuclear cells (monocytes+lymphocytes) obtained at the preceding step in culture medium (AIM-V, RPMI or IMDM type) at $10^6$ to $2.10^7$ cells/ml, possibly completed by cytokines and/or autologous serum, and culture for 5 to 10 days at 37° C. under $O_2/CO_2$ atmosphere in hydrophobic gas permeable bags, to obtain monocyte derived cells and contaminating lymphocytes;

loading the monocyte derived cells thus obtained with an exogenous nucleic acid through endocytosis targeting their mannose and/or Fc receptors, or via pinocytosis of macromolecular nucleic acid aggregates, and submission of the monocyte derived cells obtained at the preceeding step to physical stress such as electropulsation, enabling intracellular transfer of the exogenous nucleic acid into the nucleus and integration into the DNA of the nucleus.

According to an advantageous embodiment of the invention, the process comprises, after the step of electropulsation, the additional step of centrifugation of the stimulated monocyte derived cells at a temperature enabling cell preservation, for instance at 4° C., and resuspension, for instance in isotonic medium containing autologous serum.

According to another advantageous embodiment of the invention, the process comprises, after the step of electropulsation, the additional steps of:

centrifugation of the stimulated monocyte derived cells at a temperature enabling cell preservation, for instance at 4° C., and resuspension, for instance in isotonic medium containing autologous serum, and freezing at a temperature at least of -80° C. aliquots of the stimulated monocyte derived cells obtained at the preceding step, with the addition of a cryopreservative such as polyethyleneglycol, glycerol, DMSO.

The invention also relates to stimulated monocyte derived cell such as obtained by the processes described above.

The invention also relates to a method for the ex-vivo stimulation of monocytes derived cells comprising physical stress. The stimulated cells, as measured by biological effects generated, enhance the immune response in vivo after reinjection to a patient.

The invention also relates to pharmaceutical compositions comprising, as active substance, stimulated monocyte derived cells as described above, in association with a pharmaceutically acceptable vehicle.

Advantageous pharmaceutical compositions according to the invention, are in the form of sterile injectable preparations or of sterile topical preparations.

In the injectable preparation, the active substance is present in an amount such that it corresponds from about $10^7$ to about $10^{10}$ cells/kg of body weight, particularly from about $10^8$ to about $10^9$. In a topical preparation, the active substance is present in an amount of about $10^5$ to about $10^8$ cells/cm$^2$ of body surface.

In particular embodiment, the monocyte derived cells are injected repeatedly at doses of $10^7$ to $5.10^9$ at intervals of 3 days to 6 months.

The injections can eventually be first local (subcutaneous, intramuscular, mucosal, in cavities or in tissues) and then systemic (intravenous or intralymphatic).

The invention also relates to pharmaceutical compositions as described above, in the form of a vaccine comprising, as active substance, stimulated monocyte derived cells as described above, having integrated in their nucleus an exogenous nucleic acid coding for a polypeptide or protein which is immunogenic with respect to pathogens involved in the pathology to be treated.

The invention also relates to the use of stimulated monocyte derived cells of the invention, for the preparation of a medicament for the treatment of tissue repair The invention also relates to a method for the treatment of tissue repair comprising the use of stimulated monocyte derived cells as described above.

The invention also relates to the use of stimulated monocyte derived cells of the invention, for the preparation of a vaccine against tumors or infectious agents, or of a medicament for treating polypeptide or protein deficiency in a patient, said use comprising for instance the preparation of sterile flasks of stimulated monocyte derived cells suspension and their repeated local application on the injured site.

The invention also relates to a method for the vaccination against turnouts or infectious agents comprising the use of stimulated monocyte derived cells of the invention, with said stimulated monocyte derived cells having integrated in their nucleus an exogenous nucleic acid coding for a polypeptide or a protein which is immunogenic with respect to the above-mentioned tumor or infectious agent.

The invention also relates to a method for ex vivo gene therapy comprising the use of stimulated monocyte derived cells of the invention, with said stimulated monocyte derived cells having integrated in their nucleus an exogenous nucleic acid coding for a polypeptide or a protein which is deficient in a patient, said use comprising for instance the preparation of a sterile injectable suspension of stimulated monocyte derived cells and its repeated systemic and local injection.

The invention also relates to a method for the stimulation of monocyte derived cells comprising the preparation of stimulated monocyte derived cells as described above, and injection in vivo to a patient to stimulate the immune system as evidenced by release of mediators and other biological effects.

The invention will be further illustrated in the following detailed description.

Ex vivo stressing of monocytes derived cells (MDC) by physical treatment to induce a new desired stimulating biological activity.

Human blood derived mononuclear cells are grown ex vivo in culture bags in defined medium. They are submitted to specific stimuli such as electropulsation, heating at 40° C. to 50° C. or heat shock, microwaves. The intensity and length of these treatments determines the physiological status achieved by the MDC (Monocytes Derived Cells).

Before physical treatment, the differentiated MDC have eventually phagocytosed specific compounds such as drugs, nucleic acids, polypeptides, chemokines or growth factors, and are loaded with these compounds to be processed and/or released when required. They have therefore gained ex vivo new specific potential that can then be exploited therapeutically by local or systemic reinjection to the patient from whom the original blood mononuclear cells were apherized. Thus the release of various factors artificially loaded or endogenously produced by stressed MDC which are themselves in an activated status, is controlled.

Methods and culture conditions are disclosed describing the physical treatments used and the specific MDCs functionalities obtained. The beneficial effects of these cells used for the adoptive therapy of specific diseases are described.

Monocytes-Macrophages or Macrophages-Dendritic cells- grown ex vivo, are subsequently stimulated by irradiation, electropulsation, or thermal stress for purpose of gaining new therapeutic stimulating potential—generally via controlled release of various factors either artificially loaded into or endogeneously produced by MDCs.

Monocytes derived cells can be obtained in large amounts (>$10^9$ MDCs) after culture of mononuclear cells obtained from blood apheresis or from blood "buffycoats" containing peripheral blood leucocytes in plastic or hydrophobic bags (for example ethylene vinylacetate or Teflon) and in defined culture media (see PCT patent application PCT/FR96/00121).

These MDCs are differentiated after one week of culture. They are then exposed in vitro to physical stress.

In the present invention, the stress consists in the disturbance of the physical environment of the cells (change of oxygen/$CO_2$ concentration and pressure osmolality temperature change, electric stimulation, microwaves, ultrasonication . . . ) which results in temporary modification of ion fluxes, activation of intracellular kinases, stimulation of stress proteins, flux of molecules (proteins, drugs, nucleic acids) from the cytoplasm to the nucleus.

The stimulated MDCs have therefore acquired new characteristics, as described above.

TABLE 1

FACTORS RELEASED BY STRESSED STIMULATED MDC

| ENZYMES | RADICAL OXYGEN |
|---|---|
| Lyzosymes | Superoxide |
| Neutral proteases | Hydrogen peroxide |
| Plasminogen activator | Hydroxyl radical |
| Collagenase | Hypohalous acids |
| Elastase | BIOACTIVE LIPIDS |
| Angiotensin-convertase | Arachidonic acid metabolites |
| Acid hydrolases | Prostaglandins E2, F2α |
| Proteases | Prostacyclin |
| Lipases | Thromboxane |
| Ribonucleases | Leukotrienes B4, C, D and E |
| Phosphatases | Hydroxy-eicosatetraeneoic acids |
| Glycosidases | (including SRS-A) |
| Sulphatases | Platelet activating factors |
| Arginase | CYTOKINES, HORMONES |
| COMPLEMENT COMPOUNDS | Endogenous pyrogens |
| C1, 4, 2, 3 and 5 | Interleukins 1α and β$_1$ |
| Factors B and D and Properdin | Tumors necrosis factor α |
| C1 inhibitor | Interferons α and β$_1$ |
| C3b inactivator and β-1H | Interleukin 6 and 8 |
| ENZYME INHIBITORS | Chemotactic factors for |
| (Antiproteases) | Neutrophils |
| α1-antiprotease | T lymphocytes |
| Plasmin inhibitors | Monocytes |
| α2-macroglobulin | Fibroblasts |
| Plasminogen activator inhibitors | Hematopoetic Colony Stimulating |
| PROTEINS BINDING FE | Factors for |
| AND LIPIDS | Granulocyte-Macrophages |
| Acidic isoferritins | (GM-CSF) |
| Transferrin | Granulocytes (G-CSF) |
| Transcobalamin II | Macrophages (M-CSF) |
| Fibronectin | Erythropoeitin |
| Laminin | Growth factors |

TABLE 1-continued

FACTORS RELEASED BY STRESSED STIMULATED MDC

| | |
|---|---|
| Lipid transfer protein | Fibroblast growth factor |
| Thrombospondin | "platelet-derived growth factor" |
| | Transforming growth factor α and β |
| | Endothelial cell growth factor |
| | Hormones |
| | 1α, 25-Dihydroxyvitamin D3 |
| | Insulin-like activity |
| | Thymosin B4 |
| | β endorphin |
| | Adrenocorticotrophic hormone |

EXAMPLES

Four examples of ongoing developments and applications are described hereafter.

a) In a particular embodiment of the invention, MDCs are obtained after one week of culture of cells with high phagocytic activity.

These MDCs are triggered by heating 30 minutes at 45° C. to express and release growth factors, heat shock and stress proteins, chemokines and monokines. These cells added to cultures of human fibroblasts, of human osteoblasts as well as to cultures of human chondrocytes stimulate the proliferation of these different cells.

The activated MDCs are frozen in aliquots at −80° C. (in 10% DMSO, 10% autologous serum or in polyethylene glycol 10% autologous serum) and then used when needed. The concentration of polyethylene glycol can be increased after fast unfreezing of the alilquot to obtain cells included in a gel, which can be directly applied on wounds or tissues needing repair. In vivo, these triggered MDCs sustain regeneration of skin tissues presenting necrotic lesions.

The major portion of defrosted MDCs in 30% glycerol 20% autologous serum retains viability for at least 48 h in oxygenated conditions. When added at a 1/1 ratio to fibroblasts, they increase their proliferation. Application of $10^6$ MDCs onto skin punch lesions induced to nude mice is used to assess the effect of these human MDCs on the quality of cicatrisarion and of the detersion (histology).

The present invention describes in particular an effective method to induce skin wound healing by local application of autologous macropliages or MDCs prepared with the MAK Cell Processor (PCT/FR96/00121) and incorporated in an adequate pharmaceutical gel preparation. Macrophages actively initiate phagocytosis of tissue debris and contaminating bacteria. Simultaneously, they release locally for days/weeks growth factors and monokines stimulating epidermal and dermal tissue regeneration and skin repair. These monokines are measured by ELISA method.

In a particular embodiment of the invention the MDCs differentiated and recovered with a cell processor are resuspended in glucose, polyethylene glycol or sugar polymers (i.e.: Dextran derivatives, heparins or heparan sulfate, mannose-6 phosphates). These sugar or polyethylene glycol polymers allow cryopreservation of macrophage preparations aliquoted for sequential use, and after local application they stabilize by complexation of the growth factors secreted by macrophages and release them on demand. For cryopreservation of the macrophages, 4% autologous serum and 10% DMSO or polyethylene glycol can advantageously be used.

In another embodiment, macrophages are preloaded ax vivo with one or several growth factors such as PDGF, EGF, FGE . . . or a drug to increase their wound healing potential.

In a particular embodiment, autologous macrophages are replaced for therapy by an allogenic macrophage cell line such as Mono Mac 6 (Ziegler Heitbrock et al.—"Distinct patterns of differentiation induced in the monocytic cell line Mono Mac 6", J. of Leucocyte Biol., Vol. 55, January 1994), appropriately differentiated under good manufacture practice conditions.

b) In another embodiment of the invention, the MDCs prepared according to the process described have interiorized tumor antigens of interest (by phagocytosis of tumor apoptotic bodies generated from tumor cells and containing in particular mitochondria and DNA are cultured during 4 h at 37° C. with the MDCs) and are then submitted to the physical stress. Due to the induced presentation of the antigens at the same time as accessory and costimulation molecules, specific T cells are activated and do proliferate when cocultured with the MDCs. In vitro proliferation of lymphocytes is shown in the test of mixed lymphocyte proliferation.

Immunostimulation around the cells presenting the antigen of interest is demonstated by the secretion of TH1 type cytokines (IL-12, IFNγ, IL-2) in the presence of stressed MDCs.

Vaccination against the antigen of interest is shown after the injection of 1 million of these stressed antigen loaded MDCs by subcutaneous route in mice which causes potent immune response (presence of antitumor antibodies and of antitumor cytotoxic T lymphocytes).

c) In a third embodiment of the invention, MDCs are loaded with nucleic acids through endocytosis during 4 h at 37° C. of macromolecular nucleic acid mannosylated polylysine aggregates targetting their mannose receptors. After washing and resuspension at 5 millions cells/ml in isotonic sucrose medium, these cells are then submitted to short electropulsation stimuli (5 pulses of 5 msecs at 0.5 kV/cm) allowing intracellular transfer of the nucleic acid from the cytoplasm into the cell nuclei and integration in DNA. These cells are then washed and injected in animal models. The cell expression and local release for several weeks of the polypeptides coded by the nucleic acids interiorised before ex vivo physical treatment is demonstrated by ELISA and FACS analysis (fluorescence cell analysis).

Conditions for uptake of polylysine-cDNA are 0.1 µg/ml/ $10^8$ cells for 4 h at 37° C., followed by 5 square electric pulses of 5 millisec at 0.3 to 0.5 kV.

The very effective transfection ($\geq$20% efficiency and high intensity of expression) allows prolonged expression and release of the protein of interest in the extracellular medium.

This technique will prove particularly effective in the long lasting replacement therapy for the treatment of generic deficiencies, for example of Factor VIII in haemophiliacs with Factor VIII deficiency.

MDCs injected in an autologous way survive for several months in tissues where the release of factor of therapeutic interest can be measured.

d) Stimulation of monocyte derived cells by chemicals

Maturation and stimulation of MD-APC (monocyte derived-antigen presenting cells).

MATERIAL AND METHODS

Generation and Maturation of MD-APC

MD-APC are generated from total PBMC (Peripheral Blood Mononuclear Cells) obtained by apheresis and culture in AIM-V medium in the presence of GM-CSF (500 UI/ml) and IL-13 (50 ng/ml). At day 7 of the culture, double stranded RNA (d.s.RNA )(30 µg/ml) is added to the culture and the cells are incubated for another 48 hours. Phenotypic characterization is performed by flow cytometry on a FACScalibur cytofluometer using the CellQuest software (Becton Dickinson, San Jose, Calif.).

Allogenic Lymphocyte Proliferation

Serial dilutions ($10^3$ to $10^5$) of mitomycine treated MD-APC are cultured in the presence of $10^5$ allogeneic responder T cells for 4 days. T cell proliferation is measured by BrdU incorporation.

RESULTS

Phenotypic Maturation of MD-APC

Upon d.s.RNA treatment, CD40, CD80, CD86 expression increases on MD-APC. Moreover CD83, which is completely absent from untreated MD-APC is clearly expressed on more than 80% of cells cultured in the presence of d.s.RNA. In contrast, CD14 which is expressed on 70% of the untreated cells, is absent from cells treated with d.s.RNA.

Functional Maturation of MD-APC

Upon d.s.RNA treatment, 20 times less MD-APC are required to observe the same level of T cell proliferation, as compared to untreated MD-APC indicating potent immunostimulatory properties.

Cytokine Secretion

IL-12 secretion by MD-APCs is increased at least 10 to 100 fold 48 hours after addition of d.s.RNA to the culture medium, which would favor TH1 type immune responses.

What is claimed is:

1. Isolated monocyte derived cells having immunostimulating properties and presenting the following properties:
   increased release, with respect to unstimulated monocyte derived cells which have not been exposed to chemical or physical stress, of
   IL12, and
   increased presence, on their membranes, with respect to unstimulated monocyte derived cells, of the following molecules:
   MHC class I and MHC class II molecules, accessory molecule CD40 and at least one of the following activation markers CD80, CD83, and CD86.

2. Isolated monocyte derived cells having immunostimulating properties according to claim 1, loaded with exogenous compounds selected from the group consisting of drugs, proteins, growth factors and DNA coding for a protein.

3. Isolated monocyte derived cells having immunostimulating properties according to claim 1, wherein the activation markers are present in an amount of at least 1000 molecules/cells.

4. Isolated monocyte derived cells having immunostimulating properties according to claim 1, wherein the polypeptides, proteins or compounds are released in an amount higher than 1 pg/cell/hr and the activation markers are present in the range of $10^3$ to $10^5$ molecules/cell.

5. Process for conferring immunostimulating properties to macrophages, comprising the step of stimulating said macrophages by physical means selected from the group consisting of thermal stress (heating at 40° C. to 50° C. for at least 30 minutes), pressure change (from 1 bar to 10 bars), microwaves, electric shock (1 to 10 seconds at 250 mV), and electropulsation.

6. Process for the preparation of isolated monocyte derived cells having immunostimulating properties, comprising the steps:
   1) recovering blood derived mononuclear cells directly from blood apheresis or from blood bag collection, followed by optional centrifugation, to eliminate a substantial part of red blood cells, granulocytes and platelets, and collection of peripheral blood leukocytes;
   2) washing peripheral blood leukocytes obtained at the preceding steps to obtain mononuclear cells;
   3) resuspending the cells (monocytes+lymphocytes) obtained at the preceding step in culture medium (AIM-V, RPMI or IMDM type) at $10^6$ to $2 \times 10^7$ cells/ml, completed by cytokines and/or autologous serum, and culture for 5 to 10 days at 37° C. under $O_2/CO_2$ atmosphere in hydrophobic gas permeable bags, to obtain monocyte derived cells and contaminating lymphocytes;
   stimulating said monocyte derived cells by physical means selected from the group consisting of
   thermal stress (heating at 40° C. to 50° C. for at least 30 minutes), pressure change (from 1 bar to 10 bars), microwaves, electric shock (1 to 10s at 250 mV), or electropulsation for a time sufficient to induce the stimulation of the cell or integration of exogenous nucleic acid into the DNA of the monocyte derived cell.

7. Process for the preparation of isolated monocyte derived cells with immunostimulating properties, comprising the steps:
   1) recovering blood derived mononuclear cells directly from blood apheresis or from blood bag collection, followed by optional centrifugation, to eliminate a substantial part of red blood cells, granulocytes and platelets, and collection of peripheral blood leukocytes;
   2) washing peripheral blood leukocytes obtained at the preceding steps to obtain mononuclear cells;
   3) resuspending the cells (monocytes+lymphocytes) obtained at the preceding step in culture medium (RPMI or IMDM type) at $10^6$ to $2 \times 10^7$ cells/ml, possibly completed by cytokines and/or autologous serum, and culture for 5 to 10 days at 37° C. under $O_2/CO_2$ atmosphere in hydrophobic gas permeable bags, to obtain monocyte derived cells and contaminating lymphocytes;
   stimulating said monocyte derived cells by addition of chemicals, which induce IFN production said chemicals being selected from the group consisting of double stranded RNA, bacterial or mycobacterial extracts and bacterial type DNA.

8. Process for the preparation of isolated monocyte derived cells with immunostimulating properties according to claim 6, comprising, before the step of stimulating, the step of culturing of said monocyte derived cells and contaminating lymphocytes for 2 to 24 hours, in the presence of drugs, proteins or antigens to interiorize these compounds in said monocyte derived cells.

9. Process for the preparation of isolated monocyte derived cells with immunostimulating properties according to claim 6, comprising the additional step of centrifuging the isolated monocyte derived cells with immunostimulating properties at a temperature of 4° C., said temperature enabling cell preservation, and resuspension in isotonic medium containing autologous serum.

10. Process for the preparation of isolated monocyte derived cells with immunostimulating properties according to claim 6, comprising the additional steps of:
   centrifuging the isolated monocyte derived cells with immunostimulating properties at a temperature of 4° C., said temperature enabling cell preservation, and resuspending the isolated monocyte derived cells with immunostimulating properties in isotonic medium containing autologous serum, and
   freezing at a temperature of at least −80° C. aliquots of the isolated monocyte derived cells with immunostimulating properties obtained at the preceding step, adding a cryopreservative selected from the group consisting of polyethylene glycol, glycerol, and DMSO (dimethylsulfoxide).

11. Process for the preparation of isolated monocyte derived cells with immunostimulating properties comprising the steps:
   loading the monocyte derived cells obtained by claim 9 with an exogenous nucleic acid through endocytosis targeting their mannose and/or Fc receptors, or via pinocytosis of macromolecular nucleic acid aggregates, and
   submitting the monocyte derived cells obtained at the preceding step to physical stress including electropulsation from 1 to 10 pulses of 5 msecs at 0.3 to 1 kV/cm, enabling intracellular transfer of the exogenous nucleic acid into the nucleus and integration into the DNA of the nucleus.

12. Process for the preparation of isolated monocyte derived cells with immunostimulating properties comprising the steps:
   1) recovering blood derived mononuclear cells directly from blood apheresis or from blood bag collection, followed by optional centrifugation, to eliminate a substantial part of red blood cells, granulocytes and platelets, and collection of peripheral blood leukocytes;
   2) washing peripheral blood leukocytes obtained at the preceding steps to obtain mononuclear cells;
   3) resuspending the cells (monocytes+lymphocytes) obtained at the preceding step in culture medium (AIM-V, RPMI or IMDM type) at $10^6$ to $2 \times 10^7$ cells/ml, possibly completed by cytokines and/or autologous serum, and culture for 5 to 10 days at 37° C. under $O_2/CO_2$ atmosphere in hydrophobic gas permeable bags, to obtain monocyte derived cells and contaminating lymphocytes;
   loading the monocyte derived cells thus obtained with an exogenous nucleic acid through endocytosis targeting their mannose and/or Fc receptors, or via pinocytosis of macromolecular nucleic acid aggregates, and
   submitting the monocyte derived cells obtained at the preceding step to electropulsation, enabling intracellular transfer of the exogenous nucleic acid into the nucleus and integration into the DNA of the nucleus.

13. Process for the preparation of isolated monocyte derived cells with immunostimulating properties according to claim 11, comprising, before the step of loading, the step of culturing said monocyte derived cells and contaminating lymphocytes for 2 to 24 hours, in the presence of drugs, proteins or antigens to interiorize these compounds in said monocyte derived cells.

14. Process for the preparation of isolated monocyte derived cells with immunostimulating properties according to claim 12, comprising the additional step of centrifuging the monocyte derived cells with immunostimulating properties at a temperature of 4° C., said temperature enabling cell preservation, and resuspending the cells in isotonic medium containing autologous serum.

15. Process for the preparation of isolated monocyte derived cells with immunostimulating properties according to claim 12, comprising the additional steps of:

centrifuging the monocyte derived cells with immunostimulating properties at a temperature of 4° C., said temperature enabling cell preservation and resuspending the monocyte derived cells in isotonic medium containing autologous serum, and freezing at a temperature of at least −80° C. aliquots of the monocyte derived cells with immunostimulating properties obtained at the preceding step, with the addition of a cryopreservative selected from the group consisting of polyethylene glycol, glycerol, and DMSO (dimethyl-sulfoxide).

16. Pharmaceutical composition comprising, as active substance, isolated monocyte derived cells with immunostimulating properties according to claim 1, in association with a pharmaceutically acceptable vehicle.

17. Pharmaceutical composition according to claim 16, in the form of sterile injectable preparations or of sterile topical preparations.

18. Pharmaceutical composition in the form of a vaccine comprising, as active substance, isolated monocyte derived cells with immunostimulating properties according to claim 1, having integrated in their nucleus, an exogenous nucleic acid coding for a polypeptide or protein which is immunogenic.

19. Medicament comprising isolated monocyte derived cells with immunostimulating properties according to claim 1, in the form of a vaccine against tumors or infectious agents, and for treating polypeptide or protein deficiency in a patient.

* * * * *